(12) United States Patent
Kawashima et al.

(10) Patent No.: US 7,307,077 B2
(45) Date of Patent: *Dec. 11, 2007

(54) HETEROCYCLIC COMPOUND AND ANTITUMOR AGENT CONTAINING THE SAME AS EFFECTIVE INGREDIENT

(75) Inventors: Seiichiro Kawashima, Tokyo (JP); Toshiyuki Matsuno, Tokyo (JP); Shinichi Yaguchi, Tokyo (JP); Hiroya Sasahara, Tokyo (JP); Tetsuo Watanabe, Tokyo (JP)

(73) Assignee: Zenyaku Kogyo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/478,647

(22) Filed: Jul. 3, 2006

(65) Prior Publication Data

US 2006/0247232 A1  Nov. 2, 2006

Related U.S. Application Data

(63) Continuation of application No. 10/475,094, filed as application No. PCT/JP02/04227 on Apr. 26, 2002, now Pat. No. 7,071,189.

(30) Foreign Application Priority Data

Apr. 27, 2001  (JP) ............................ 2001-132250

(51) Int. Cl.
   - C07D 413/14 (2006.01)
   - A61K 31/506 (2006.01)
   - A61K 31/5377 (2006.01)
   - A61P 35/00 (2006.01)

(52) U.S. Cl. .................. 514/231.5; 544/112; 544/114

(58) Field of Classification Search ............... 544/112, 544/114; 514/231.5
   See application file for complete search history.

(56) References Cited

U.S. PATENT DOCUMENTS

| | | | |
|---|---|---|---|
| 3,308,122 A | 3/1967 | Tolkmith | |
| 5,489,591 A | 2/1996 | Kobayashi et al. | |
| 5,852,019 A | 12/1998 | Ejima et al. | |
| 6,251,900 B1 | 6/2001 | Kawashima et al. | |
| 7,071,189 B2 * | 7/2006 | Kawashima et al. | 514/231.5 |
| 2004/0116421 A1 | 6/2004 | Kawashima et al. | |
| 2006/0009440 A1 | 1/2006 | Kawashima et al. | |

FOREIGN PATENT DOCUMENTS

| | | |
|---|---|---|
| EP | 0 240 854 A1 | 10/1987 |
| EP | 0 640 599 B1 | 3/1995 |
| JP | 49-17677 | 5/1974 |
| JP | 56-55302 | 5/1981 |
| JP | 62-240673 | 10/1987 |
| WO | WO 93/17009 | 9/1993 |
| WO | WO 96/10024 | 4/1996 |
| WO | 99/5138 | 2/1999 |
| WO | 00/43385 | 7/2000 |
| WO | WO 02/088112 A1 | 11/2002 |
| WO | WO 2004/037812 A1 | 5/2004 |
| WO | WO 2005/095389 A1 | 10/2005 |

OTHER PUBLICATIONS

U.S. Appl. No. 11/404,078, filed Apr. 14, 2006, Yaguchi, et al.
Bonny L. Johnson, et al., "Hexamethylmelamine in Alkylating Agent-Resistant Ovarian Carcinoma", Cancer, vol. 42, Nov. 1978, pp. 2157-2161.
Toshiyuki Matsuno, et al., "Synthesis and Aromatase-Inhibitory Activity of Imidazolyl-1,3,5-triazine Derivatives", Chem. Pharm. Bull., vol. 45, No. 2, Feb. 1997, pp. 291-296.
Shin-Ichi Yaguchi, et al., The 64th Annual Meeting Abstract of the Japanese Cancer Association, W-018, and PA2-0729-PA20732, Sep. 2005 (with English abstracts).
Shin-ichi Yaguchi, et al., The 96th Annual Meeting Abstract of American Association for Cancer Research, 1691, C65 and C239, Nov. 2005, 6 pages.

(Continued)

*Primary Examiner*—Venkataraman Balasubramanian
(74) *Attorney, Agent, or Firm*—Oblon, Spivak, McClelland, Maier & Neustadt, P.C.

(57) ABSTRACT

The present invention relates to heterocyclic compounds represented by the formula I or pharmaceutically acceptable salts thereof and antitumor agents containing the heterocyclic compounds as effective components:

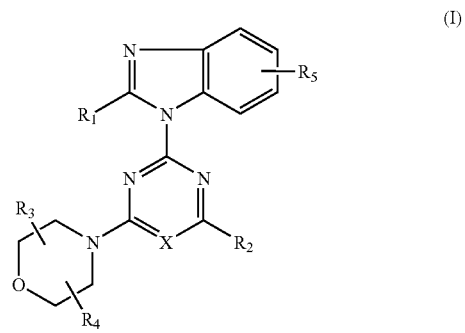

(I)

wherein X represents nitrogen atom or CH; $R_1$ represents $CH_nF_{3-n}$ (wherein n is 1 or 2), hydroxy $C_1$-$C_6$ alkyl, $NHR_6$ [wherein $R_6$ represents hydrogen atom or COR (wherein R represents hydrogen atom, $C_1$-$C_6$ alkyl or $C_1$-$C_6$ alkoxy)]; $R_2$ represents morpholino (which may be substituted with one to four $C_1$-$C_6$ alkyl), thiomorpholino, piperidino, pyrrolidinyl (which may be substituted with hydroxy $C_1$-$C_6$ alkyl), oxazolidinyl (which may be substituted with one or two $C_1$-$C_6$ alkyl) or tetrahydro-1,4-thiazin-1-oxo-4-yl; $R_3$ and $R_4$ each represent hydrogen atom or $C_1$-$C_6$ alkyl; and $R_5$ represents hydrogen atom, amino or hydroxyl.

16 Claims, No Drawings

OTHER PUBLICATIONS

Shin-ichi Yaguchi, et al., "Antitumor Activity of ZSTK474, a New Phosphatidylinositol 3-Kinase Inhibitor", Journal of the National Cancer Institute, vol. 98, No. 8, Apr. 19, 2006, pp. 545-556.

Shin-ichi Yaguchi, et al., "In Vitro Cytotoxicity of Imidazolyt-1,3,5-triazine Derivatives", Biol. Pharm. Bull., vol. 20, No. 6, Jun. 1997, pp. 698-700.

Yuichi Iino, et al., "Antitumor Effects of SEF19, a New Nonsteroidal Aromatase Inhibitor, on 7,12-Dimethylbenz [a] anthracene-Induced Mammary Tumors in Rats", Anticancer Research, vol. 18, 1998, pp. 171-176.

Takao Yamori, et al., "A novel Phosphatidylinositol 3-kinase Inhibitor, ZSTK474, and its Preclinical Activity", the 10th International Symposium on Cancer Chemotherapy, Jan. 2006, 2 pages.

U.S. Appl. No. 10/594,994, filed Sep. 29, 2006, Kawashima, et al.

Chem. Pharm. Bull vol. 48, No. 11, pp. 1778-1781, 2000.

Toshiyuki Matsuno, et al., Chem. Pharm. Bull., vol. 48, No. 11, pp. 1778-1781, 2000.

Cecil Textbook of Medicine, Edited by Bennet, J.C., and Plum F., 20th Edition, vol. 1, pp. 1004-1010 (1996).

Connor, et al., Fundamental and Applied Toxicology, vol. 30(1):93-101 (1996).

Coley, et al. Anticancer Research 16(4A); pp. 1851-1855 (1996).

* cited by examiner

HETEROCYCLIC COMPOUND AND ANTITUMOR AGENT CONTAINING THE SAME AS EFFECTIVE INGREDIENT

Cross-Reference to Related Applications

The present application is a continuation of U.S. application Ser. No. 10/475,094 filed on Oct. 27, 2003, now U.S. Pat. No. 7,071,189, which is a 371 application of PCT/JP02/04227 filed Apr. 26, 2002.

TECHNICAL FIELD

The present invention relates to heterocyclic compounds represented by the formula I or pharmaceutically acceptable salts thereof and antitumor agents containing the heterocyclic compounds as effective components:

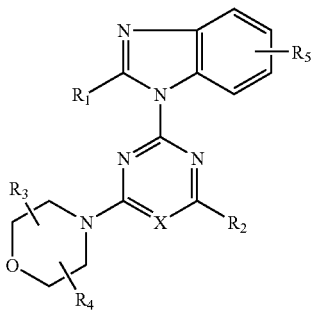

wherein X represents nitrogen atom or CH; $R_1$ represents $CH_nF_{3-n}$ (wherein n is 1 or 2), hydroxy $C_1$-$C_6$ alkyl, $NHR_6$ [wherein $R_6$ represents hydrogen atom or COR (wherein R represents hydrogen atom, $C_1$-$C_6$ alkyl or $C_1$-$C_6$ alkoxy)]; $R_2$ represents morpholino (which may be substituted with one to four $C_1$-$C_6$ alkyl), thiomorpholino, piperidino, pyrrolidinyl (which may be substituted with hydroxy $C_1$-$C_6$ alkyl), oxazolidinyl (which may be substituted with one or two $C_1$-$C_6$ alkyl) or tetrahydro-1,4-thiazin-1-oxo-4-yl; $R_3$ and $R_4$ each represent hydrogen atom or $C_1$-$C_6$ alkyl; and $R_5$ represents hydrogen atom, amino or hydroxyl.

BACKGROUND ART s-Triazine (1,3,5-triazine) and pyrimidine derivatives have been researched in the fields of synthetic resins, synthetic fibers, dyes and agricultural chemicals and a number of such compounds have been synthesized. In the field of pharmaceuticals, researches have been made with respect to antitumor, anti-inflammatory, analgesic and antispasmodic activities. Especially, hexamethylmelamine (HMM) is well-known which has been developed as analogue of antitumor agent triethylenemelamine (TEM) [B. L. Johnson et al. Cancer, 42: 2157-2161 (1978)].

TEM is known as alkylating agent and is an s-triazine derivative having cytotoxic antitumor activity. HMM has been marketed in Europe under the indications for the treatment of ovarian and small cell lung cancers, and its action on solid cancers have attractive.

Among the s-triazine derivatives, imidazolyl-s-triazine derivatives which exhibit cytotoxic and selective aromatase inhibitory activities have been proposed as medicine for estrogen-dependent diseases such as endometriosis, multi-cystic ovarium, mastosis, endometrium carcinoma and breast cancer (PCT international publication WO93/17009).

However, there is still room for improvement on HMM with respect to its antitumor spectrum and intensity of antitumor activities against solid cancers. As to imidazolyl-s-triazine derivatives, they are limitative in application since they exhibit considerably higher aromatase inhibitory activities than their cytotoxic activities and application of them to cancerous patients other than those who suffer from estrogen-dependent diseases may lead to development of secondary effects such as menstrual disorders due to lack of estrogen. There are still, therefore, strong demands on medicines with no aromatase inhibitory activities and effective for solid cancers.

DISCLOSURE OF THE INVENTION

Under such situations and in order to expand antitumor activities of HMM and to decrease aromatase inhibitory activities of imidazolyl-s-triazine derivatives, we, the inventors, carried out intensive studies to find out s-triazine and pyrimidine-derivatives with substitution of benzimidazole (PCT international publications WO99/05138 and WO00/43385).

However, since even these compounds have not contented anti-tumor activities, we further developed the studies to find out that heterocyclic compounds with specific substituents at position 2 of benzimidazole ring and represented by the formula I exhibit by far improved antitumor activities, thus completing the present invention.

The terms used for definition of letters in the formula I, by which the heterocyclic compounds of the present invention are represented, will be defined and exemplified in the following.

The term "$C_1$-$C_6$" refers to a group having 1 to 6 carbon atoms unless otherwise indicated.

The "$C_1$-$C_6$ alkyl" refers to a straight- or branched-chain alkyl group such as methyl, ethyl, n-propyl, isopropyl, n-butyl, tert-butyl, n-pentyl or n-hexyl.

The "hydroxy $C_1$-$C_6$ alkyl" refers to the above-mentioned "$C_1$-$C_6$ alkyl" with any of the carbon atoms coupled to hydroxy group.

The "$C_1$-$C_6$ alkoxy" refers to a straight- or branched-chain alkoxy group such as methoxy, ethoxy, n-propoxy, isopropoxy, n-butoxy, tert-butoxy, n-pentyloxy or n-hexyloxy.

The compounds according to the present invention may be as follows, though the present invention is not limited to these compounds.

2-(2-difluoromethylbenzimidazol-1-yl)-4-(cis-2,3-dimethylmorpholino)-6-morpholinopyrimidine 2-(2-difluoromethylbenzimidazol-1-yl)-4,6-dimorpholinopyrimidine 2-(2-difluoromethylbenzimidazol-1-yl)-4-morpholino-6-thiomorpholinopyrimidine 2-(2-difluoromethylbenzimidazol-1-yl)-4-(trans-2,3-dimethylmorpholino)-6-morpholinopyrimidine 2-(2-difluoromethylbenzimidazol-1-yl)-4-(2,2-dimethylmorpholino)-6-morpholinopyrimidine 2-(2-difluoromethylbenzimidazol-1-yl)-4-(2-methylmorpholino)-6-morpholinopyrimidine 2-(2-difluoromethylbenzimidazol-1-yl)-4-morpholino-6-[2,2,5(R)-trimethylmorpholino]pyrimidine 2-(2-difluoromethylbenzimidazol-1-yl)-4-morpholino-6-[2,2,5(S)-trimethylmorpholino]pyrimidine 4-(cis-2,3-dimethylmorpholino)-2-(2-fluoromethylbenzimidazol-1-yl)-6-morpholinopyrimidine 2-(2-aminobenzimidazol-1-yl)-4-(cis-2,3-dimethylmorpholino)-6-morpholinopyrimidine
2-(2-aminobenzimidazol-1-yl)-4-(trans-2,3-dimethylmorpholino)-6-morpholinopyrimidine
4-(cis-2,3-dimethylmorpholino)-2-(2-hydroxymethylbenzimidazol-1-yl)-6-morpholinopyrimidine
4-(cis-2,3-dimethylmorpholino)-2-(2-hydroxymethylbenzimidazol-1-yl)-6-piperidinopyrimidine
4-(cis-2,3-dimethylmorpholino)-2-(2-hydroxymethylbenzimidazol-1-yl)-6-(2-hydroxymethylpyrrolidin-1-yl)pyrimidine
2-(6-amino-2-difluoromethylbenzimidazol-1-yl)-4,6-dimorpholinopyrimidine
2-(6-amino-2-difluoromethylbenzimidazol-1-yl)-4-(cis-2,3-dimethylmorpholino)-6-morpholinopyrimidine
2-(2-difluoromethyl-5-hydroxybenzimidazol-1-yl)-4,6-dimorpholinopyrimidine
2-(2-difluoromethyl-4-hydroxybenzimidazol-1-yl)-4-(2,2-dimethylmorpholino)-6-morpholinopyrimidine
2-(2,4-diaminobenzimidazol-1-yl)-4-(2,2-dimethylmorpholino)-6-morpholinopyrimidine
2-(2,4-diaminobenzimidazol-1-yl)-4,6-dimorpholinopyrimidine
2-(2-amino-4-hydroxybenzimidazol-1-yl)-4-(2,2-dimethylmorpholino)-6-morpholinopyrimidine
2-(2-difluoromethylbenzimidazol-1-yl)-4-(cis-2,3-dimethylmorpholino)-6-morpholino-1,3,5-triazine
2-(2-difluoromethylbenzimidazol-1-yl)-4-(trans-2,3-dimethylmorpholino)-6-morpholino-1,3,5-triazine
2-(2-difluoromethylbenzimidazol-1-yl)-4-(2,2-dimethylmorpholino)-6-morpholino-1,3,5-triazine
2-(2-difluoromethylbenzimidazol-1-yl)-4-morpholino-6-thiomorpholino-1,3,5-triazine
2-(2-difluoromethylbenzimidazol-1-yl)-4-(2-methylmorpholino)-6-morpholino-1,3,5-triazine
2-(2-difluoromethylbenzimidazol-1-yl)-4-(trans-2,5-dimethylmorpholino)-6-morpholino-1,3,5-triazine
2-(2-difluoromethylbenzimidazol-1-yl)-4,6-dimorpholino-1,3,5-triazine
2-(2-difluoromethylbenzimidazol-1-yl)-4-morpholino-6-[2,2,5(R)-trimethylmorpholino]-1,3,5-triazine
2-(2-difluoromethylbenzimidazol-1-yl)-4-morpholino-6-(tetrahydro-1,4-thiazin-1-oxo-4-yl)-1,3,5-triazine
2-(2-acetylaminobenzimidazol-1-yl)-4,6-dimorpholino-1,3,5-triazine
2-(2-acetylaminobenzimidazol-1-yl)-4-(trans-2,3-dimethylmorpholino)-6-morpholinopyrimidine
2-(2-formylaminobenzimidazol-1-yl)-4,6-dimorpholino-1,3,5-triazine
2-(2-propionylaminobenzimidazol-1-yl)-4-(trans-2,3-dimethylmorpholino)-6-morpholino-1,3,5-triazine
2-(trans-2,3-dimethylmorpholino)-4-(2-formylaminobenzimidazol-1-yl)-6-morpholino-1,3,5-triazine
4-(trans-2,3-dimethylmorpholino)-2-(2-formylaminobenzimidazol-1-yl)-6-morpholinopyrimidine
2-(cis-2,6-dimethylmorpholino)-4-(2-formylaminobenzimidazol-1-yl)-6-morpholino-1,3,5-triazine
2-(2-methoxycarbonylaminobenzimidazol-1-yl)-4,6-dimorpholino-1,3,5-triazine
2-(2-aminobenzimidazol-1-yl)-4,6-dimorpholino-1,3,5-triazine
2-(2-aminobenzimidazol-1-yl)-4-(trans-2,3-dimethylmorpholino)-6-morpholino-1,3,5-triazine
2-(2-aminobenzimidazol-1-yl)-4-(cis-2,3-dimethylmorpholino)-6-piperidino-1,3,5-triazine
2-(2-difluoromethylbenzimidazol-1-yl)-4-morpholino-6-piperidino-1,3,5-triazine
2-(2-difluoromethylbenzimidazol-1-yl)-4-(trans-2,3-dimethylmorpholino)-6-(2-hydroxymethylpyrrolidin-1-yl)-1,3,5-triazine
2-(6-amino-2-difluoromethylbenzimidazol-1-yl)-4-(2,2-dimethylmorpholino)-6-morpholino-1,3,5-triazine
2-(6-amino-2-difluoromethylbenzimidazol-1-yl)-4-(cis-2,3-dimethylmorpholino)-6-morpholino-1,3,5-triazine
2-(4-amino-2-difluoromethylbenzimidazol-1-yl)-4,6-dimorpholino-1,3,5-triazine
2-(2-difluoromethyl-5-hydroxybenzimidazol-1-yl)-4-(2,3-cis-dimethylmorpholino)-6-morpholino-1,3,5-triazine
2-(2-difluoromethyl-6-hydroxybenzimidazol-1-yl)-4-(2,2-dimethylmorpholino)-6-morpholino-1,3,5-triazine
2-(2-difluoromethyl-5-hydroxybenzimidazol-1-yl)-4-(2,2-dimethyloxazolidin-3-yl)-6-morpholino-1,3,5-triazine
2-(2-difluoromethyl-4-hydroxybenzimidazol-1-yl)-4,6-dimorpholino-1,3,5-triazine
2-(2-difluoromethyl-4-hydroxybenzimidazol-1-yl)-4-(2,2-dimethylmorpholino)-6-morpholino-1,3,5-triazine
2-(2,4-diaminobenzimidazol-1-yl)-4-(2,2-dimethylmorpholino)-6-morpholino-1,3,5-triazine
2-(2,4-diaminobenzimidazol-1-yl)-4,6-dimorpholino-1,3,5-triazine
2-(2-amino-4-hydroxybenzimidazol-1-yl)-4-(2,2-dimethylmorpholino)-6-morpholino-1,3,5-triazine The compounds of the present invention may have asymmetric carbon atoms in the structure. It is to be understood that isomers due to such asymmetric carbon atom or combination (racemate) of any of the isomers are included in the category of the compounds according to the present invention.

Furthermore, the compounds of the present invention may be in the form of pharmaceutically acceptable acid addition salts. The appropriate acid addition salts which can be used include, for example, inorganic salts such as hydrochloride, sulfate, hydrobromide, nitrate and phosphate as well as organic acid salts such as acetate, oxalate, propionate, glycolate, lactate, pyruvate, malonate, succinate, maleate, fumarate, malate, tartarate, citrate, benzoate, cinnamate, methanesulfonate, benzenesulfonate, p-toluenesulfonate and salicylate.

Production Processes

The compounds of the present invention represented by the formula I may be prepared by, as shown in the following reaction formula, reacting cyanuric chloride or 2,4,6-trichloropyrimidine (compound II) as starting material with benzimidazole compound (compound V), morpholine compound (compound VI) and R$_2$H (compound VII) successively in the order named.

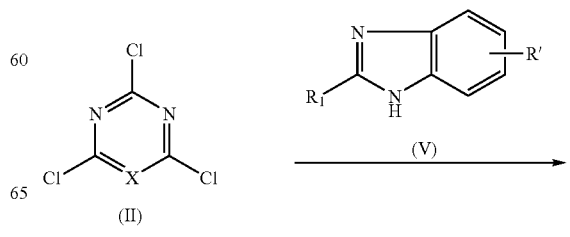

-continued

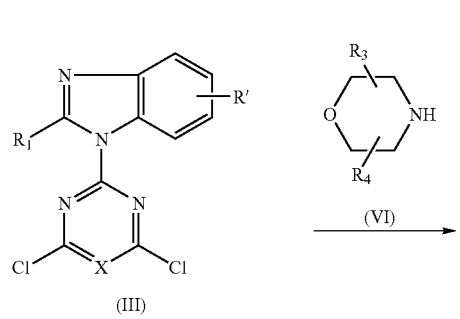

(III)

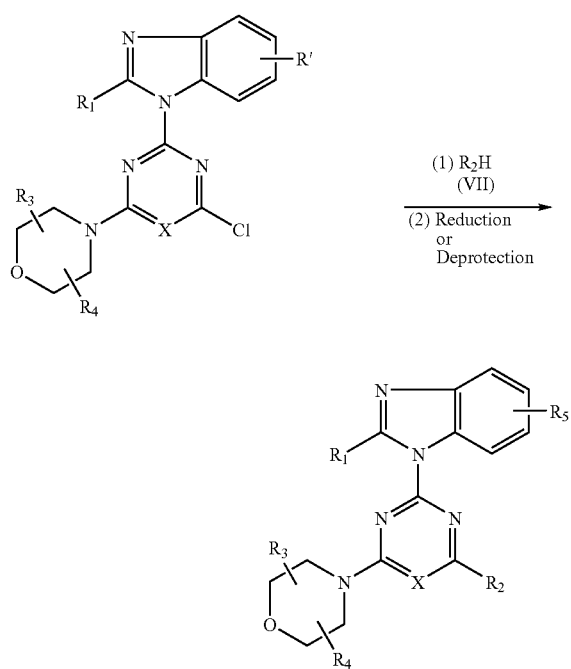

(IV)

wherein $R_1$, $R_2$, $R_3$, $R_4$, $R_5$ and X are as defined above and R' represents hydrogen atom, nitro or tert-butyldimethylsilyloxy.

Next, the respective production processes will be described.

1) Production Process (i) of Intermediate III:

Reaction Formula (i)

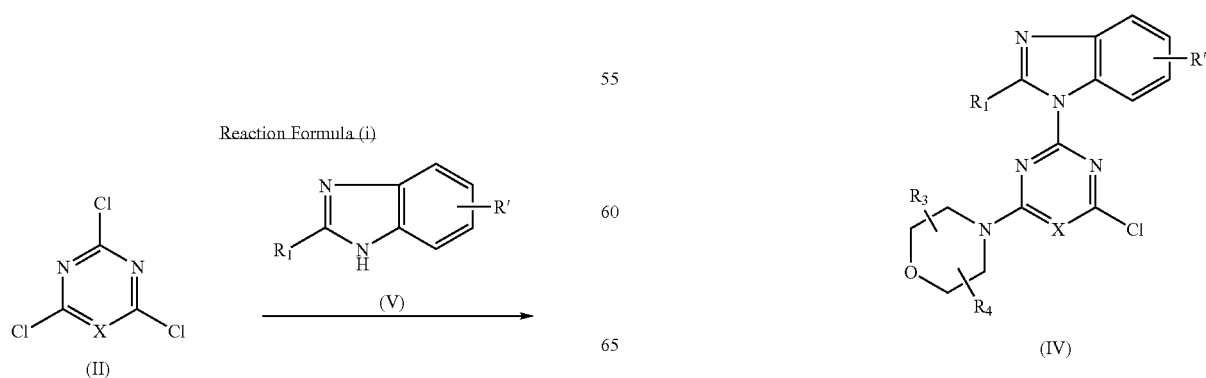

-continued

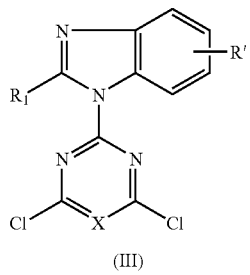

(III)

wherein $R_1$, R' and X are as defined above.

In a solvent, cyanuric chloride or 2,4,6-trichloropyrimidine (compound II) is reacted with benzimidazole compound (compound V) in the presence of hydrogen chloride trapping agent to obtain the intermediate III.

The hydrogen chloride trapping agent used in this reaction may be, for example, sodium hydroxide, potassium hydroxide, sodium carbonate, potassium carbonate, triethylamine or pyridine. The solvent used may be acetone, toluene, hexane, xylene, dioxane, tetrahydrofuran or dichloroethane or N,N-dimethylformamide (DMF).

In this reaction, 0.5-1.2 moles of the compound V is used per mole of the compound II in the presence of 0.5-1.2 moles of the hydrogen chloride trapping agent. The reaction is made at the temperature of −15° C.--5° C. for 0.5-2 hours, and further at the room temperature for 5-50 hours.

It is to be noted that the compound V may be also used as the hydrogen chloride trapping agent.

2) Production Process (ii) of Intermediate IV

Reaction Formula (ii)

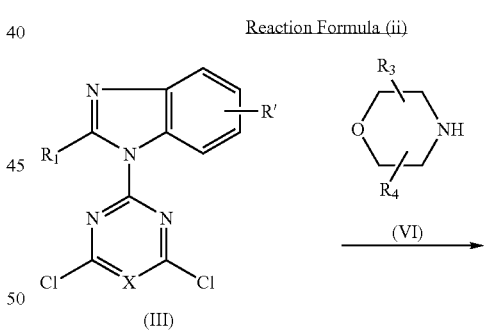

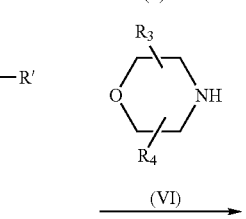

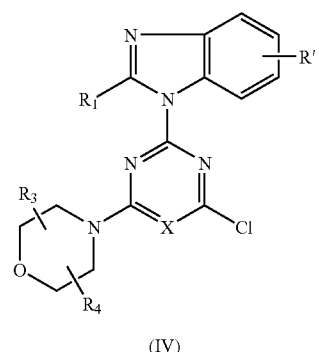

(IV)

wherein $R_1$, $R_3$, $R_4$, R' and X are as defined above.

In the solvent, the intermediate III obtained in the above-mentioned production process (i) is reacted with morpholine compound (compound VI) in the presence of hydrogen chloride trapping agent to obtain the intermediate IV. The hydrogen chloride trapping agent used in this reaction may be the same as those in the above-mentioned production process (i). The solvent used may be DMF, acetone, toluene, xylene, dichloroethane or dichloromethane.

In this reaction, 0.5-1.2 moles of the compound VI is used per mole of the intermediate III and in the presence of 0.5-3 moles of the hydrogen chloride trapping agent. The reaction is made at the temperature of −5° C.-0° C. for 0.5-3 hours, and further at the room temperature for 5-50 hours.

It is to be noted that the compound VI may be also used as the hydrogen chloride trapping agent.

3) Production Process (iii) of the Compound I

Reaction Formula (iii)

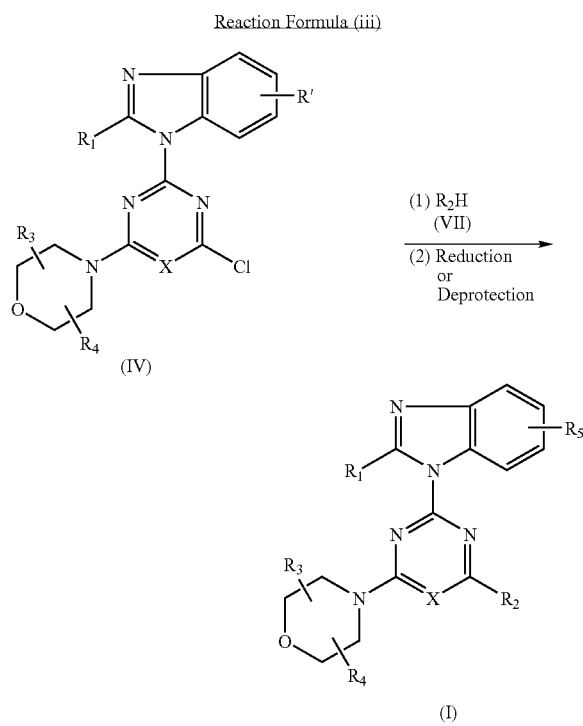

(IV)

(1) $R_2H$
(VII)
(2) Reduction or Deprotection (I)

wherein $R_1$, $R_2$, $R_3$, $R_4$, $R_5$, R' and X are as defined above.

In the solvent, the intermediate IV obtained in the above-mentioned production process (ii) is reacted with $R_2H$ (compound VII) in the presence of hydrogen chloride trapping agent to obtain the compound I according to the present invention.

The hydrogen chloride trapping agent used in this reaction may be the same as those in the above-mentioned production process (i). The solvent used may be DMF, dimethyl sulfoxide (DMSO), xylene or dichloroethane.

In this reaction, 1-5 moles of $R_2H$ (the compound VII) is used per mole of the intermediate IV at the temperature between room temperature and 140° C. for 0.1-16 hours. In the case of the reaction in the presence of the hydrogen chloride trapping agent, 1-5 moles of the hydrogen chloride trapping agent is used per mole of the intermediate IV. It is to be noted that the compound VII may be also used as the hydrogen chloride trapping agent.

In such production of the compound I and when the compounds VI and VII are the same, the production processes (ii) and (iii) may be carried out in a single step to obtain the compound I. In this case, the reaction conditions are as mentioned in the above with respect to the production process (ii) except that 2-10 moles of the compound VI or VII is used per mole of the compound III and that the reaction is made at the temperature of −10° C.-5° C. for 0.1-5 hours, and further at the temperature between room temperature and 120° C. for 3-50 hours.

When the compound V, VI or VII used in the production process (i), (ii) or (iii) has lower reactivity, it is preferable that the production process is carried out after treatment with sodium hydride. In the case of sodium hydride being used, 1.0-1.2 moles of sodium hydride is used per mole of the starting material in the production process (compound II, III or IV).

When $R_1$ has hydroxyl or when $R_5$ is hydroxyl, the reaction is carried out, using benzimidazole compound with hydroxyl protected by alkylsilyl group such as tert-butyldimethylsilyl according to ordinary method; in a final step, the protective group is removed to obtain the aimed compound. When $R_5$ is amino, the reaction is carried out, using benzimidazole with substitution of nitro; in a final step, catalytic reduction is carried out by ordinary method under a hydrogen atmosphere to obtain the aimed compound.

The above-mentioned production processes (i), (ii) and (iii) may be carried out in any exchanged order. In such a case, the reaction conditions may be varied to an extent obvious to ordinary experts in the art.

The resultant products in the above-mentioned respective production processes may be separated and purified, as needs demand, by ordinary method such as extraction, condensation, neutralization, filtration, re-crystallization or column chromatography.

Acid-addition salts of the compounds I of the present invention may be prepared according to various methods well-known in the art. The appropriate acids used include, for example, inorganic acids such as hydrochloric, sulfuric, hydrobromic, nitric or phosphoric acid, and organic acids such as acetic, oxalic, propionic, glycolic, lactic, pyruvic, malonic, succinic, maleic, fumaric, malic, tartaric, citric, benzoic, cinnamic, methanesulfonic, benzenesulfonic, p-toluenesulfonic or salicylic acid.

Next, antitumor activities of the compounds I of the present invention will be described. Numbers of the tested compounds in the tests 1 and 2 correspond to those in Examples referred to hereinafter.

Comparative compounds used were the following s-triazine-series antitumor agents or medicines for estrogen-dependent diseases:

Compound A: 2-(benzimidazol-1-yl)-4-(trans-2,3-dimethylmorpholino)-6-morpholinopyrimidine (a typical compound disclosed in the international publication WO99/05138)

Compound B: 2-(2-methylbenzimidazol-1-yl)-4,6-dimorpholino-1,3,5-triazine (a typical compound disclosed in the international publication WO99/05138)

Compound C: 2-(imidazol-1-yl)-4,6-dimorpholino-1,3,5-triazine (typical compound disclosed in the international publication WO93/17009)

Compound D: hexamethylmelamine (HMM)

Test 1

Used in the test were MCF-7 cells which were established from human breast cancer and were cultured routinely under the conditions of 37° C. and 5% $CO_2$, in MEM medium supplemented with 10% fetal calf serum, 25 mM of HEPES and 0.1 mg/ml of kanamycin. The MCF-7 cells in a logarithmic growth phase were treated with trypsin/EDTA to prepare single cell suspension adjusted to $4.0 \times 10^4$ cells/ml in MEM medium (supplemented with 10% fetal calf serum, 25 mM of HEPES and 0.1 mg/ml of kanamycin). Test compounds were dissolved in DMSO and diluted with RPMI 1640 medium (supplemented with 10% fetal calf serum, 25 mM of HEPES and 0.1 mg/ml of kanamycin) to a concentration of $2.0 \times 10^{-4}$-$2.0 \times 10^{-9}$ M.

The cell suspension was filled in a 96-wells microplate at a rate of 0.1 ml per well and was cultured for 24 hours so as to make the cells adhered to the microplate. Then, it was added with 0.1 ml of the sample solution and cultured at 37° C. for 72 hours in 5% $CO_2$.

50% Growth inhibition concentrations ($GI_{50}$ µM) were calculated from growth inhibitions at various sample concentrations. The results are as shown in Table 1.

TABLE 1

| test compound | $GI_{50}(\mu M)$ |
|---|---|
| compound 1 | 0.11 |
| compound 2 | 0.21 |
| compound 3 | 0.38 |
| compound 4 | 0.18 |
| compound 5 | 0.22 |
| compound 6 | 0.29 |
| compound 8 | 0.32 |
| compound 9 | 0.20 |
| compound 10 | 0.13 |
| compound 11 | 0.20 |
| compound 12 | 0.39 |
| compound 14 | 0.16 |
| compound 15 | 0.13 |
| compound 16 | 0.35 |
| compound 17 | 0.12 |
| compound 18 | 0.18 |
| compound 19 | 0.09 |
| compound 20 | 0.22 |
| compound 21 | 0.34 |
| compound 22 | 0.23 |
| compound 23 | 0.19 |
| compound 25 | 0.19 |
| compound 26 | <0.04 |
| compound 27 | 0.16 |
| compound 29 | 0.25 |
| compound 30 | 0.25 |
| compound 31 | 0.24 |
| compound 32 | 0.18 |
| compound 33 | 0.08 |
| compound 34 | 0.08 |
| compound 35 | 0.14 |
| compound 36 | 0.29 |
| compound 37 | 0.09 |
| compound 38 | 0.03 |
| compound 39 | 0.06 |
| compound 40 | 0.21 |
| compound A | 2.2 |
| compound B | 3.7 |
| compound C | 20 |
| compound D | >100 |

The above test results clearly revealed that the compounds of the present invention exhibit by far superior antitumor activities on human breast cancer cells than the known comparative compounds A, B, C and D.

The compounds of the present invention were also effective in vitro tests using human non small cell lung cancer cells and human colonic cancer cells and therefore positively expected is application of the compounds according to the present invention on treatment of various human solid cancers.

Test 2

Human colon cancer WiDr was grown as subcutaneous tumor in mutant BALA/c nude mice. 2-mm-cube tumor fragments were transplanted subcutaneously into left flank of the nude mice. When the tumor reached logarithmic growth phase, mice were divided randomly into test groups consisting five mice per group. The samples prepared by dissolving test compounds in physiological saline solution or suspending them in 1% hydroxypropyl cellulose (HPC), using an agate mortar, were intraperitoneally administered at a rate of 200 mg/kg, once a day and six times a week in total, for two weeks. Major and minor axes of the tumor mass were measured on a daily basis to calculate tumor volume. The tumor volume at each measured day was divided by that at the start day of the sample administration to calculate relative tumor growth rate; and the relative tumor growth rate of the treated groups (T) and that of the control group (C) were used to calculate T/C (%). Cases where T/C (%) of the last day was less than 50% and U-assay of Mann-Whitney revealed significant difference with one-sided risk rate of 1% were judged to be effective (+). The results are as shown in Table 2.

TABLE 2

| test compound | judgment |
|---|---|
| compound 14 | + |
| compound 19 | + |
| compound 22 | + |
| compound 31 | + |
| compound 32 | + |
| compound 33 | + |
| compound A | − |

Next, description will be made on ways of administration, appearances and administered amount of the compounds of the present invention where they are applied to mammals, especially to human.

The compounds of the present invention may be administered orally or parenterally. In oral administration, the compounds may be in the appearance of tablets, coated tablets, powders, granules, capsules, microcapsules, syrups and the like; and in parenteral administration, in the appearance of injections which may include soluble freeze-drying appearance, suppositories and the like. In the preparation of these appearances, pharmaceutically acceptable excipient, binders, lubricants, disintegrators, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

The dosage for humans may depend on the condition of the disease to be treated, the age and weight of the patient and the like. A daily dosage for an adult may be in the range of from 100 to 1,000 mg and may be given in divided doses 2 or 3 times a day.

BEST MODE FOR CARRYING OUT THE INVENTION

Next, the present invention is more specifically illustrated with reference to the following Examples of the compounds. It is to be, however, noted that the present invention is not limited to these Examples.

EXAMPLE 1

2-(2-difluoromethylbenzimidazol-1-yl)-4-(cis-2,3-dimethylmorpholino)-6-morpholinopyrimidine (Compound 1)

(1) 0.84 g (5 mmol) of 2-difluoromethylbenzimidazole dissolved in DMF (25 ml) was added and reacted with 60% sodium hydride (0.24 g, 6 mmol) at room temperature for 30 minutes. This suspension was added to a solution of 2,4,6-trichloropyrimidine (0.92 g, 5 mmol) dissolved in DMF (25 ml) and stirred at room temperature for 1.5 hours. The reaction solution was poured into water and the resulting precipitates were recrystallized from methanol to obtain 0.98 g (yield: 62%) of 4,6-dichloro-2-(2-difluoromethylbenzimidazol-1-yl)pyrimidine.

(2) 0.32 g (1.0 mmol) of 4,6-dichloro-2-(2-difluoromethylbenzimidazol-1-yl)pyrimidine, 0.16 g (1.0 mmol) of cis-2,3-dimethylmorpholine hydrochloride and 0.3 g (2.2 mmol) of anhydrous potassium carbonate were added to DMF (10 ml) and stirred at room temperature for 16 hours. The reaction solution was poured into water and extracted with ethyl acetate. The separated organic layer was washed with water and dried over anhydrous magnesium sulfate. The solvent was removed under reduced pressure and the residue was purified by silica gel column chromatography to obtain 0.33 g (yield: 84%) of 4-chloro-2-(2-difluoromethylbenzimidazol-1-yl)-6-(cis-2,3-dimethylmorpholino)pyrimidine.

(3) 0.33 g (0.8 mmol) of the obtained 4-chloro-2-(2-difluoromethylbenzimidazol-1-yl)-6-(cis-2,3-dimethylmorpholino)pyrimidine dissolved in morpholine (0.70 g, 8.0 mmol) was stirred at 70° C. for 1 hour. The solvent was removed under the reduced pressure from the reaction mixture and the residue was purified by silica gel column chromatography to obtain 0.326 g (yield: 90%) of the titled compound as colorless crystals.

Melting point: 167-169° C.

NMR(CDCl$_3$) δ: 1.37(3H, d, J=7 Hz), 1.38(3H, d, J=7 Hz), 3.3-4.2(14H, m), 5.47(1H, s), 7.3-7.5(2H, m), 7.51(1H, t, J=53 Hz), 7.8-8.0(1H, m), 8.2-8.3(1H, m)

MS m/z: 444(M$^+$)

In accordance with the procedure of the Example 1, the following compounds were prepared from the corresponding starting materials.

2-(2-difluoromethylbenzimidazol-1-yl)-4,6-dimorpholinopyrimidine (compound 2)

Melting point: 201-202° C.

NMR (CDCl$_3$) δ: 3.63(8H, t, J=5 Hz), 3.83(8H, t, J=5 Hz), 5.51(1H, s), 7.3-7.4(2H, m), 7.51(1H, t, J=53 Hz), 7.8-7.9 (1H, m), 8.2-8.3(1H, m)

MS m/z: 416(M$^+$)

2-(2-difluoromethylbenzimidazol-1-yl)-4-morpholino-6-thiomorpholinopyrimidine (compound 3)

Melting point: 173-175° C.

NMR(CDCl$_3$) δ: 2.71(4H, t, J=5 Hz), 3.63(4H, t, J=5 Hz), 3.83 (4H, t, J=5 Hz), 4.03 (4H, t, J=5 Hz), 5.49 (1H, s), 7.3-7.4(2H, m), 7.50(1H, t, J=53 Hz), 7.8-7.9(1H, m), 8.3-8.4 (1H, m)

MS m/z: 432(M$^+$)

2-(2-difluoromethylbenzimidazol-1-yl)-4-(trans-2,3-dimethylmorpholino)-6-morpholinopyrimidine (compound 4)

Melting point: 172-174° C.

NMR(CDCl$_3$) δ: 1.22(3H, d, J=7 Hz), 1.23(3H, d, J=7 Hz), 3.2-4.1(14H, m), 5.47(1H, s), 7.3-7.5(2H, m), 7.51(1H, t, J=53 Hz), 7.8-8.0(1H, m), 8.2-8.3(1H, m)

MS m/z: 444(M$^+$)

2-(2-difluoromethylbenzimidazol-1-yl)-4-(2,2-dimethylmorpholino)-6-morpholinopyrimidine (compound 5)

Melting point: 149-152° C.

NMR(CDCl$_3$) δ: 1.30(6H, s), 3.50(2H, s), 3.5-3.9(12H, m) 5.48(1H, s), 7.3-7.5(2H, m), 7.50(1H, t, J=53 Hz), 7.8-8.0(1H, m), 8.2-8.3(1H, m)

MS m/z: 444(M$^+$)

2-(2-difluoromethylbenzimidazol-1-yl)-4-(2-methylmorpholino)-6-morpholinopyrimidine (compound 6)

Melting point: 126-131° C.

NMR(CDCl$_3$) δ: 1.29(3H, d, J=6 Hz), 2.7-2.9(1H, m), 3.0-3.2(1H, m), 3.6-4.2(13H, m), 5.51(1H, s), 7.3-7.5(2H, m), 7.51(1H, t, J=53 Hz), 7.8-8.0(1H, m), 8.2-8.3(1H, m)

MS m/z: 430(M$^+$)

2-(2-difluoromethylbenzimidazol-1-yl)-4-morpholino-6-[2,2,5(R)-trimethylmorpholino]pyrimidine (compound 7)

Melting point: 113-116° C.

NMR(CDCl$_3$) δ: 1.2-1.4(9H, m), 3.0-3.1(1H, d, J=13 Hz), 3.5-4.1(11H, m), 4.2-4.4(1H, m), 5.46(1H, s), 7.3-7.5(1H, s), 7.51(1H, t, J=53 Hz), 7.8-8.0(1H, m), 8.2-8.3(1H, m)

MS m/z: 458(M$^+$)

2-(2-difluoromethylbenzimidazol-1-yl)-4-morpholino-6-[2,2,5(S)-trimethylmorpholino]pyrimidine (compound 8)

Melting point: 113-116° C.

NMR(CDCl$_3$) δ: 1.2-1.4(9H, m), 3.0-3.1(1H, d, J=13 Hz), 3.5-4.1(11H, m), 4.2-4.4(1H, m), 5.46(1H, s), 7.3-7.5(1H, s), 7.51(1H, t, J=53 Hz), 7.8-8.0(1H, m), 8.2-8.3(1H, m)

MS m/z: 458(M$^+$)

4-(cis-2,3-dimethylmorpholino)-2-(2-fluoromethylbenzimidazol-1-yl)-6-morpholinopyrimidine (compound 9)

Melting point: 163-165° C.

NMR(CDCl$_3$) δ: 1.36(3H, d, J=5 Hz), 1.39(3H, d, J=5 Hz), 3.3-3.5(1H, m), 3.6-4.2(13H, m), 5.46(1H, s), 5.97(2H, d, J=47 Hz), 7.3-7.4(2H, m), 7.8-7.9(1H, m), 8.2-8.3(1H, m)

MS m/z: 426(M$^+$)

EXAMPLE 2

2-(2-aminobenzimidazol-1-yl)-4-(cis-2,3-dimethylmorpholino)-6-morpholinopyrimidine In accordance with the procedure of the Example 1 except that 2-difluoromethylbenzimidazole in (1) of the Example 1 was replaced by 2-aminobenzimidazole, 27 mg (yield: 90%) of the titled compound was obtained as colorless crystals.

Melting point: 129-133° C.

NMR(CDCl$_3$) δ: 1.20(3H, d, J=7 Hz), 1.23(3H, d, J=7 Hz), 3.2-4.2(14H, m), 5.43(1H, s), 6.62(2H, brs), 7.0-7.4 (3H, m), 8.1-8.2(1H, m)

MS m/z: 409(M$^+$)

In accordance with the procedure of the Example 2, the following compound was prepared from the corresponding starting material.

2-(2-aminobenzimidazol-1-yl)-4-(trans-2,3-dimethylmorpholino)-6-morpholinopyrimidine Melting point: 118-123° C.

NMR(CDCl$_3$) δ: 1.36(3H, d, J=7 Hz), 1.39(3H, d, J=7 Hz), 3.3-4.2(14H, m), 5.42(1H, s), 6.63(2H, brs), 7.0-7.4 (3H, m), 8.1-8.2(1H, m)

MS m/z: 409(M$^+$)

EXAMPLE 3

4-(cis-2,3-dimethylmorpholino)-2-(2-hydroxymethylbenzimidazol-1-yl)-6-morpholinopyrimidine (Compound 10)

In accordance with the procedure of the Example 1 except that 2-difluoromethylbenzimidazole in (1) of the Example 1 was replaced by 2-tert-butyldimethylsilyloxymethyl-benzimidazole, 1.62 g (yield: 80%) of 2-(2-tert-butyldimethylsilyloxymethylbenzimidazol-1-yl)-4-(cis-2,3-dimethylmorpholino)-6-morpholinopyrimidine was obtained. 1.62 g (3.0 mmol) of the obtained compound dissolved in THF (10 ml) was added with tetrabutylammoniumfluoride (1.18 g, 4.5 mmol) and stirred at room temperature for 30 minutes. The reaction solution was poured into water and dealt with in accordance with the procedure of (2) of the Example 1 and purified by column chromatography to obtain 0.86 g (yield: 67%) of the titled compound as colorless crystals.

Melting point: 125-128° C.

NMR(CDCl$_3$) δ: 1.37(3H, t, J=7 Hz), 1.39(3H, d, J=7 Hz), 3.3-4.2(14H, m), 5.13(2H, s), 5.46(1H, s), 7.2-7.4(2H, m), 7.7-7.8(1H, m), 8.2-8.3(1H, m)

MS m/z: 424(M$^+$)

In accordance with the procedure of the Example 3, the following compounds were prepared from the corresponding starting materials.

4-(cis-2,3-dimethylmorpholino)-2-(2-hydroxymethylbenzimidazol-1-yl)-6-piperidinopyrimidine (compound 11)

Melting point: 141-143° C.

NMR(CDCl$_3$) δ: 1.36(3H, t, J=7 Hz), 1.39(3H, d, J=7 Hz), 1.70(6H, m), 3.3-3.5(1H, m), 3.6-4.2(9H, m), 4.76(1H, s), 5.13(2H, s), 5.46(1H, s), 7.2-7.4(2H, m), 7.7-7.8(1H, m), 8.2-8.4(1H, m)

MS m/z: 422(M$^+$)

4-(cis-2,3-dimethylmorpholino)-2-(2-hydroxymethylbenzimidazol-1-yl)-6-(2-hydroxymethylpyrrolidin-1-yl)pyrimidine (compound 12)

Melting point: 104-108° C.

NMR(CDCl$_3$) δ: 1.37(3H, t, J=7 Hz), 1.39(3H, d, J=7 Hz), 2.0-2.2(4H, m), 3.3-4.4(10H, m), 4.9-5.2(2H, m), 5.30 (1H, d, J=2 Hz), 5.4-5.5(1H, m), 7.3-7.4(2H, m), 7.7-7.8(1H, m), 8.2-8.3(1H, m)

MS m/z: 438(M$^+$)

EXAMPLE 4

2-(2-difluoromethylbenzimidazol-1-yl)-4-(cis-2,3-dimethylmorpholino)-6-morpholino-1,3,5-triazine (Compound 13)

(1) 11.8 g (50 mmol) of 2,4-dichloro-6-morpholino-1,3,5-triazine, 8.41 g (50 mmol) of 2-difluoromethylbenzimidazole and 55.3 g (400 mmol) of anhydrous potassium carbonate added to DMF (250 ml) were stirred at room temperature for 16 hours. The reaction solution was poured into water and the resulting precipitates were washed with DMF and ethanol to obtain 15.7 g (yield: 86%) of 4-chloro-2-(2-difluoromethylbenzimidazol-1-yl)-6-morpholino-1,3,5-triazine.

(2) 0.36 g (0.98 mmol) of the obtained 4-chloro-2-(2-difluoromethylbenzimidazol-1-yl)-6-morpholino-1,3,5-triazine, 0.16 g (1.0 mmol) of cis-2,3-dimethylmorpholine hydrochloride and 0.3 g (2.2 mmol) of anhydrous potassium carbonate added to DMF (10 ml) were stirred at room temperature for 16 hours. The reaction solution was poured into water and extracted with ethyl acetate. The separated organic layer was washed with water and dried over anhydrous magnesium sulfate. The solvent was removed under reduced pressure and the residue was purified by silica gel column chromatography to obtain 0.38 g (yield: 87%) of the titled compound as colorless crystals.

Melting point: 207-210° C.

NMR(CDCl$_3$) δ: 1.34(3H, d, J=7 Hz), 1.41(3H, d, J=7 Hz), 3.3-3.5(1H, m), 3.7-4.0(11H, m), 4.4-4.6(2H, m), 7.3-7.5(2H, m), 7.57(1H, t, J=53 Hz), 7.8-8.0(1H, m), 8.2-8.3 (1H, m)

MS m/z: 445(M$^+$)

In accordance with the procedure of the Example 4, the following compounds were prepared from the corresponding starting materials.

2-(2-difluoromethylbenzimidazol-1-yl)-4-(trans-2,3-dimethylmorpholino)-6-morpholino-1,3,5-triazine (compound 14).

Melting point: 135-138° C.

NMR(CDCl$_3$): 1.23(3H, d, J=6 Hz), 1.24(3H, d, J=6 Hz), 3.1-3.4(1H, m), 3.5-4.1(11H, m), 4.3-4.7(2H, m), 7.3-8.0 (4H, m), 8.3-8.4(1H, m)

MS m/z: 445(M$^+$)

2-(2-difluoromethylbenzimidazol-1-yl)-4-(2,2-dimethylmorpholino)-6-morpholino-1,3,5-triazine (compound 15)

Melting point: 176-178° C.

NMR(CDCl$_3$) δ: 1.29(6H, s), 3.6-3.9(14H, m), 7.3-8.0 (4H, m), 8.3-8.4(1H, m)

MS m/z: 445(M$^+$)

2-(2-difluoromethylbenzimidazol-1-yl)-4-morpholino-6-thiomorpholino-1,3,5-triazine (compound 16)

Melting point: 215-217° C.

NMR(CDCl$_3$) δ: 2.71(4H, t, J=5 Hz), 3.80(4H, t, J=5 Hz), 3.87(4H, t, J=5 Hz), 4.18(4H, t, J=5 Hz), 7.3-7.5(2H, m), 7.55(1H, t, J=53 Hz), 7.8-7.9(1H, m), 8.3-8.4(1H, m)

MS m/z: 433(M$^+$)

2-(2-difluoromethylbenzimidazol-1-yl)-4-(2-methylmorpholino)-6-morpholino-1,3,5-triazine (compound 17)

Melting point: 188-191° C.

NMR(CDCl$_3$) δ: 1.28(3H, d, J=6 Hz), 2.7-2.9(1H, m), 3.0-3.3(1H, m), 3.5-4.1(11H, m), 4.5-4.6(2H, m), 7.3-7.5 (2H, m), 7.56(1H, t, J=53 Hz), 7.8-8.0(1H, m), 8.2-8.4(1H, m)

MS m/z: 431(M$^+$)

2-(2-difluoromethylbenzimidazol-1-yl)-4-(trans-2,5-dimethylmorpholino)-6-morpholino-1,3,5-triazine (compound 18)

Melting point: 166-169° C.

NMR(CDCl$_3$) δ: 1.31(3H, d, J=7 Hz), 1.39(3H, d, J=7 Hz), 3.4-4.3 (13H, m), 4.6-4.8 (1H, m), 7.3-7.5 (2H, m), 7.58 (1H, t, J=7 Hz), 7.8-8.0(1H, m), 8.2-8.3(1H, m)

MS m/z: 445(M$^+$)

2-(2-difluoromethylbenzimidazol-1-yl)-4,6-dimorpholino-1,3,5-triazine (compound 19)

Melting point: 211-214° C.
NMR(CDCl$_3$) δ: 3.79(8H, t, J=4 Hz), 3.88(8H, t, J=4 Hz), 7.3-7.4(2H, m), 7.56(1H, t, J=53 Hz), 7.88(1H, d, J=7 Hz), 8.32(1H, d, J=7 Hz)
MS m/z: 417(M$^+$)
2-(2-difluoromethylbenzimidazol-1-yl)-4-morpholino-6-[2,2,5(R)-trimethylmorpholino]-1,3,5-triazine (compound 20)

Melting point: 169-171° C.
NMR(CDCl$_3$) δ: 1.2-1.4(9H, m), 3.0-3.2(1H, m), 3.5-4.1 (10H, m), 4.29(1H, d, J=13 Hz), 4.6-4.8(1H, m), 7.3-7.8(3H, m), 7.8-8.0(1H, m), 8.2-8.4(1H, m)
MS m/z: 459(M$^+$)

EXAMPLE 5

2-(2-difluoromethylbenzimidazol-1-yl)-4-morpholino-6-(tetrahydro-1,4-thiazin-1-oxo-4-yl)-1,3,5-triazine (Compound 21)

0.61 g (1.4 mmol) of 2-(2-difluoromethylbenzimidazol-1-yl)-4-morpholino-6-thiomorpholino-1,3,5-triazine dissolved in dichloromethane (20 ml) was added with m-chloroperbenzoic acid (0.35 g, 2.0 mmol) and stirred at room temperature for 16 hours. The reaction solution was poured into water and extracted with ethyl acetate. The separated organic layer was washed with water and dried over anhydrous magnesium sulfate. The solvent was removed under reduced pressure and the residue was purified by silica gel column chromatography to obtain 0.27 g (yield: 42%) of the titled compound as colorless crystals.

Melting point: 225-226° C.
NMR(CDCl$_3$) δ: 2.7-2.9(2H, m), 2.9-3.0(2H, m), 3.7-4.0 (8H, m), 4.1-4.3(2H, m), 4.6-4.8(2H, m), 7.4-7.5(2H, m), 7.52(1H, t, J=53 Hz), 7.8-7.9(1H, m), 8.3-8.4(1H, m)
MS m/z: 449(M$^+$)

EXAMPLE 6

2-(2-acetylaminobenzimidazol-1-yl)-4,6-dimorpholino-1,3,5-triazine (Compound 22)

(1) 9.32 g (70 mmol) of 2-aminobenzimidazole dissolved in DMF (300 ml) was added and reacted with 60% sodium hydride (2.80 g, 70 mmol) at room temperature for 30 minutes. This suspension was added to a solution of 14.3 g (50 mmol) of 2-chloro-4,6-dimorpholino-1,3,5-triazine dissolved in DMF (200 ml) and stirred at room temperature for 2 hours. The reaction solution was poured into water and the resulting precipitates were washed with water and methanol to obtain 17.7 g (yield: 93%) of 2-(2-aminobenzimidazol-1-yl)-4,6-dimorpholino-1,3,5-triazine.

(2) 0.38 g (1.0 mmol) of 2-(2-aminobenzimidazol-1-yl)-4,6-dimorpholino-1,3,5-triazine and 0.24 g (4.0 mmol) of acetic acid were added to and further 0.83 g (4.0 mmol) of DCC was added to chloroform (5 ml) and stirred at room temperature for 4 hours. The reaction solution was poured into water and extracted with ethyl acetate. The separated organic layer was washed with water and dried over anhydrous magnesium sulfate. The solvent was removed under reduced pressure and the residue was purified by silica gel column chromatography to obtain 0.31 g (yield: 73%) of the titled compound as colorless crystals.

Melting point: 243-245° C.
NMR(CDCl$_3$) δ: 2.65(3H, s), 3.8-4.0(16H, m), 7.2-7.4 (2H, m), 7.6-7.7(1H, m), 8.2-8.3(1H, m), 12.15(1H, s)
MS m/z: 424(M$^+$)

In accordance with the procedure of the Example 6, the following compounds were prepared from the corresponding starting materials.

2-(2-acetylaminobenzimidazol-1-yl)-4-(trans-2,3-dimethylmorpholino)-6-morpholinopyrimidine (compound 23)

Melting point: 150-153° C.
NMR(CDCl$_3$) δ: 1.22(3H, d, J=7 Hz), 1.25(3H, d, J=7 Hz), 2.67(3H, m), 3.2-3.4(1H, m), 3.6-4.3(13H, m), 5.43 (1H, s), 7.1-7.3(2H, m), 7.6-7.7 (1H, m), 8.2-8.3(1H, m), 12.12(1H, s)
MS m/z: 451(M$^+$)
2-(2-formylaminobenzimidazol-1-yl)-4,6-dimorpholino-1,3,5-triazine (compound 24)

Melting point: 221-223° C.
NMR(CDCl$_3$) δ: 3.7-4.0(16H, m), 7.2-7.4(2H, m), 7.5-7.6(1H, m), 8.2-8.3(1H, m), 9.46(1H, d, J=10 Hz), 10.75 (1H, d, J=10 Hz)
MS m/z: 410(M$^+$)
2-(2-propionylaminobenzimidazol-1-yl)-4-(trans-2,3-dimethylmorpholino)-6-morpholino-1,3,5-triazine (compound 25)

Melting point: 166-168° C.
NMR(CDCl$_3$) δ: 1.26(3H, t, J=7 Hz), 1.35(3H, d, J=6 Hz), 1.42(3H, d, J=6 Hz), 3.06(2H, q, J=7 Hz), 3.3-3.5(1H, m), 3.7-4.0(11H, m), 4.3-4.5(2H, m), 7.2-7.3(2H, m), 7.6-7.7(1H, m), 8.2-8.3(1H, m), 12.20(1H, s)
MS m/z: 466(M$^+$)
2-(trans-2,3-dimethylmorpholino)-4-(2-formylaminobenzimidazol-1-yl)-6-morpholino-1,3,5-triazine (compound 26)

Melting point: 189-191° C.
NMR(CDCl$_3$) δ: 1.35(3H, d, J=6.6 Hz), 1.42(3H, d, J=6.6 Hz), 3.4-3.5(1H, m), 3.7-4.0(11H, m), 4.3-4.5(2H, m), 7.2-7.3(2H, m), 7.6-7.7 (1H, m), 8.2-8.3(1H, m), 9.46(1H, d, J=10 Hz), 11.78(1H, d, J=10 Hz)
MS m/z: 438(M$^+$)
4-(trans-2,3-dimethylmorpholino)-2-(2-formylaminobenzimidazol-1-yl)-6-morpholinopyrimidine (compound 27)

Melting point: 143-146° C.
NMR(CDCl$_3$) δ: 1.39 (3H, d, J=7 Hz), 1.41 (3H, d, J=7 Hz), 3.3-3.5(1H, m), 3.6-3.7(4H, m), 3.8-4.2(9H, m), 5.44 (1H, s), 7.2-7.4(2H, m), 7.59(1H, d, J=9 Hz), 8.26(1H, d, J=9 Hz), 9.48(1H, d, J=10 Hz), 11.77(1H, d, J=10 Hz)
MS m/z: 437(M$^+$)
2-(cis-2,6-dimethylmorpholino)-4-(2-formylaminobenzimidazol-1-yl)-6-morpholino-1,3,5-triazine (compound 28)

Melting point: 242-244° C.
NMR(CDCl$_3$) δ: 1.2-1.4(6H, m), 2.6-2.9(2H, m), 3.6-4.0 (10H, m), 4.3-4.6(2H, m), 7.2-7.4(2H, m), 7.58(1H, d, J=7 Hz), 8.30(1H, d, J=7 Hz), 9.46(1H, d, J=10 Hz), 11.81(1H, d, J=10 Hz)
MS m/z: 438(M$^+$)

EXAMPLE 7

2-(2-methoxycarbonylaminobenzimidazol-1-yl)-4,6-dimorpholino-1,3,5-triazine (Compound 29)

0.19 g (0.50 mmol) of 2-(2-aminobenzimidazol-1-yl)-4,6-dimorpholino-1,3,5-triazine synthesized in (1) of the Example 6 and 60% sodium hydride (24 mg, 0.60 mmol)

added to DMF (2 ml) were reacted at room temperature for 1 hour. The reaction mixture was added and reacted with 0.040 ml (0.55 mmol) of chloromethylformate at room temperature for 16 hours. The reaction solution was poured into water and extracted with methyl acetate. The organic layer was separated, washed with water and dried over anhydrous magnesium sulfate. The solvent was removed under reduced pressure and the residue was purified by silica gel column chromatography to obtain 100 mg (yield: 46%) of the titled compound as colorless crystals.

Melting point: 206-209° C.
NMR(CDCl$_3$) δ: 3.8-3.9(19H, m), 7.2-7.4(2H, m), 7.71 (1H, d, J=8 Hz), 8.26(1H, d, J=9 Hz), 12.19(1H, brs)
MS m/Z: 440(M$^+$)

EXAMPLE 8

2-(6-amino-2-difluoromethylbenzimidazol-1-yl)-4-(2,2-dimethylmorpholino)-6-morpholino-1,3,5-triazine (Compound 32)

(1) 49.4 g (210 mmol) of 2,4-dichloro-6-morpholino-1,3,5-triazine, 44.8 g (210 mmol) of 2-difluoromethyl-5-nitrobenzimidazole and 34.5 g of potassium carbonate were added to acetone (700 ml) and stirred at room temperature for 16 hours. The reaction solution was poured into water and the resultant precipitate was washed with water and acetone to obtain 61.4 g (yield: 71%) of a mixture of 4-chloro-2-(2-difluoromethyl-5-nitrobenzimidazol-1-yl)-6-morpholino-1,3,5-triazine with 4-chloro-2-(2-difluoromethyl-6-nitrobenzimidazol-1-yl)-6-morpholino-1,3,5-triazine.

(2) 0.72 g of the obtained mixture, 0.32 g (2.1 mmol) of 2,2-dimethylmorpholine hydrochloride and 0.6 g of potassium carbonate were added to DMF (10 ml) and stirred at room temperature for 16 hours. The reaction solution was poured into the water and extracted with ethyl acetate. The organic layer was separated, washed with water and dried over anhydrous magnesium sulfate to obtain 0.76 g (yield: 89%) of a mixture of 2-(2-difluoromethyl-5-nitrobenzimidazol-1-yl)-4-(2,2-dimethylmorpholino)-6-morpholino-1,3,5-triazine with 2-(2-difluoromethyl-6-nitrobenzimidazol-1-yl)-4-(2,2-dimethylmorpholino)-6-morpholino-1,3,5-triazine.

(3) 0.76 g of the mixture obtained in (2) above was suspended in ethanol (50 ml) and catalytically reduced in the presence of 0.10 g of 10% Pd—C as catalyst at room temperature in hydrogen atmosphere. Insoluble was filtered out and the solvent was removed under reduced pressure and the residue was purified by silica gel column chromatography to obtain 0.65 g (yield: 92%) of the titled compound as colorless crystals.

Melting point: 226-227° C. (decomp.)
NMR(CDCl$_3$) δ: 1.28(6H, s), 3.6-3.8(16H, m), 6.7-6.8 (1H, m), 7.2-7.7 (3H, m)
MS m/z: 460(M$^+$)

In accordance with the procedure of the Example 8, the following compounds were prepared from the corresponding starting materials.

2-(6-amino-2-difluoromethylbenzimidazol-1-yl)-4-(2,3-cis-dimethylmorpholino)-6-morpholino-1,3,5-triazine (compound 33)

Melting point: 220-222° C. (decomp.)
NMR(CDCl$_3$) δ: 1.22(3H, d, J=9 Hz), 1.26(3H, d, J=9 Hz), 3.1-3.4(1H, m), 3.5-4.1 (11H, m), 4.3-4.5(1H, m), 4.5-4.7(1H, m), 6.77(1H, dd, J=2 Hz, 9 Hz), 7.49(1H, t, J=54 Hz), 7.62(1H, d, J=9 Hz), 7.64(1H, d, J=2 Hz)
MS m/z: 460(M$^+$)

2-(4-amino-2-difluoromethylbenzimidazol-1-yl)-4,6-dimorpholino-1,3,5-triazine (compound 34)

Melting point: 214-216° C. (decomp.)
NMR(CDCl$_3$) δ: 3.7-3.9(16H, m), 4.48(2H, brs), 6.63 (1H, d, J=8 Hz), 7.21(1H, t, J=8 Hz), 7.55(1H, t, J=54 Hz), 7.64(1H, d, J=8 Hz)
MS m/z: 432(M$^+$)

EXAMPLE 9

2-(6-amino-2-difluoromethylbenzimidazol-1-yl)-4,6-dimorpholinopyrimidine (Compound 35)

In accordance with the procedure of the Example 1 except that 2-difluoromethylbenzimidazole in (1) of the Example 1 was replaced by 2-difluoro-6-nitrobenzimidazole, a mixture of 2-(2-difluoromethyl-5-nitrobenzimidazol-1-yl)-4,6-dimorpholinopyrimidine with 2-(2-difluoromethyl-6-nitrobenzimidazol-1-yl)-4,6-dimorpholinopyrimidine was obtained. In accordance with the procedure of (3) of the Example 8, using 0.92 g (2.0 mmol) of this mixture, 0.76 g (yield: 88%) of the titled compound was obtained as colorless crystals.

Melting point: 218-219° C. (decomp.)
NMR(CDCl$_3$) δ: 3.6-3.9(18H, m), 5.49(1H, s), 6.76(1H, dd, J=2 Hz, 9 Hz), 7.43(1H, t, J=54 Hz), 7.51(1H, d, J=2 Hz), 7.64(1H, d, J=9 Hz)
MS m/z: 431(M$^+$)

In accordance with the procedure of the Example 9, the following compound was prepared from the corresponding starting material.

2-(6-amino-2-difluoromethylbenzimidazol-1-yl)-4-(2,3-cis-dimethylmorpholino)-6-morpholinopyrimidine (compound 36)

Melting point: 155-158° C. (decomp.)
NMR(CDCl$_3$) δ: 1.21(3H, d, J=7 Hz), 1.22(3H, d, J=7 Hz), 3.1-3.4(1H, m), 3.6-4.1(11H, m), 5.45(1H, s), 6.78(1H, dd, J=2 Hz, 9 Hz), 7.44(1H, t, J=54 Hz), 7.52(1H, d, J=2 Hz), 7.65(1H, d, J=9 Hz)
MS m/z: 459(M$^+$)

EXAMPLE 10

2-(2-difluoromethyl-5-hydroxybenzimidazol-1-yl)-4-(2,3-cis-dimethylmorpholino)-6-morpholino-1,3,5-triazine (Compound 37)

In accordance with the procedure of the Example 4 except that 2-difluoromethylbenzimidazole in (1) of the Example 4 was replaced by 2-difluoromethyl-5-tert-butyldimethyl-silyloxybenzimidazole, obtained was 2-(2-difluoromethyl-5-tert-butyldimethylsilyloxybenzimidazol-1-yl)-4-(2,3-cis-dimethylmorpholino)-6-morpholino-1,3,5-triazine. 120 mg (0.22 mmol) of the obtained compound dissolved in THF (2 ml) was added with a solution of tetrabutylammoniumfluoride (1 M) in THF (0.5 ml) and stirred at room temperature for 30 minutes. The reaction solution was poured into water and extracted with ethyl acetate. The separated organic layer was washed with water and dried over anhydrous magnesium sulfate. The solvent was removed under reduced pressure and the residue was purified by silica gel column chromatography to obtain 75 mg (yield: 79%) of the titled compound as colorless crystals.

Melting point: 170-175° C. (decomp.)

NMR(CDCl₃) δ: 1.1-1.3(6H, m), 3.1-3.4 (1H, m), 3.5-4.1 (11H, m), 4.3-4.7 (2H, m), 7.04 (1H, d, J=9 Hz), 7.29 (1H, d, J=3 Hz) 7.54(1H, dt, J=4 Hz, 54 Hz), 8.18(1H, dd, J=3 Hz, 9 Hz)

MS m/z: 461(M⁺)

In accordance with the procedure of the Example 10, the following compounds were prepared from the corresponding starting materials.

2-(2-difluoromethyl-4-hydroxybenzimidazol-1-yl)-4-(2,2-dimethylmorpholino)-6-morpholino-1,3,5-triazine (compound 38)

Melting point: 228-231° C. (decomp.)

NMR(CDCl₃) δ: 1.28(6H, s), 3.6-3.9(14H, m), 6.8-6.9 (2H, m), 7.2-7.9(3H, m)

MS m/z: 461(M⁺)

2-(2-difluoromethyl-5-hydroxybenzimidazol-1-yl)-4-(2,2-dimethyloxazolidin-3-yl)-6-morpholino-1,3,5-triazine (compound 39)

Melting point: 239-243° C. (decomp.)

NMR(CDCl₃) δ: 1.59(6H, s), 3.8-4.0(10H, m), 5.25(2H, s), 7.03(1H, d, J=9 Hz), 7.29(1H, s), 7.56(1H, t, J=54 Hz), 8.20(1H, d, J=9 Hz)

MS m/z: 447(M⁺)

EXAMPLE 11

2-(2-difluoromethyl-5-hydroxybenzimidazol-1-yl)-4,6-dimorpholinopyrimidine (Compound 40)

In accordance with the procedure of the Example 1 except that 2-difluoromethylbenzimidazole in (1) of the Example 1 was replaced by 2-difluoromethyl-5-tert-butyldimethylsilyloxybenzimidazole, obtained was 2-(2-difluoromethyl-5-tert-butyldimethylsilyloxybenzimidazol-1-yl)-4,6-dimorpholinopyrimidine. 0.55 g (1.0 mmol) of the obtained compound dissolved in THF (10 ml) was added with a solution of tetrabutylammoniumfluoride (1 M) in THF (2 ml) and stirred at room temperature for 30 minutes. The reaction solution was poured into water and extracted with ethyl acetate. The separated organic layer was washed with water and dried over anhydrous magnesium sulfate. The solvent was removed under reduced pressure and the residue was purified by silica gel column chromatography to obtain 0.40 g (yield: 93%) of the titled compound as colorless crystals.

Melting point: 223-226° C. (decomp.)

NMR(CDCl₃) δ: 3.5-4.0(16H, m), 5.50(1H, s), 7.00(1H, dd, J=2 Hz, 9 Hz), 7.29(1H, d, J=9 Hz), 7.49(1H, t, J=53 Hz), 8.01(1H, d, J=9 Hz)

MS m/z: 432(M⁺)

EXAMPLE 12

2-(2-aminobenzimidazol-1-yl)-4-(cis-2,3-dimethylmorpholino)-6-morpholinopyrimidine hydrochloride (Compound 30)

1.23 g (3.0 mmol) of 2-(2-aminobenzimidazol-1-yl)-4-(cis-2,3-dimethylmorpholino)-6-morpholinopyrimidine obtained in the Example 2 and dissolved in 2N hydrochloric acid (3.0 ml) was condensed under reduced pressure and the resultant crystals were filtered out to obtain 1.20 g (yield: 90%) of the titled compound as colorless crystals.

Melting point: 151-155° C.

NMR(D₂O) δ: 1.07(3H, d, J=6 Hz), 1.22(3H, d, J=6 Hz), 3.0-4.1(14H, m), 5.51(1H, s), 7.0-7.3(3H, m), 7.7-7.9(1H, m)

MS m/z: 410[M+1]⁺

In accordance with the procedure of the Example 12, the following compound was obtained from the corresponding starting material.

2-(2-aminobenzimidazol-1-yl)-4-(trans-2,3-dimethylmorpholino)-6-morpholinopyrimidine hydrochloride (compound 31)

Melting point: 141-145° C.

NMR(D₂O) δ: 1.30(3H, d, J=7 Hz), 1.38(3H, d, J=7 Hz), 3.2-3.5(5H, m), 3.6-4.1(9H, m), 5.58(1H, s), 7.07(1H, t, J=8 Hz), 7.19 (1H, d, J=8 Hz), 7.28 (1H, t, J=8 Hz), 7.74 (1H, d, J=8 Hz)

MS m/z: 410[M+1]⁺

CAPABILITY OF EXPLOITATION IN INDUSTRY

The compounds of the present invention exhibit apparently by far strong antitumor activities with no aromatase inhibitory activities in comparison with conventional s-triazine and pyrimidine derivatives and can be applied to treatment on solid cancers.

What is claimed is:

1. A composition comprising a compound represented by formula I, and a pharmaceutically acceptable diluent or carrier:

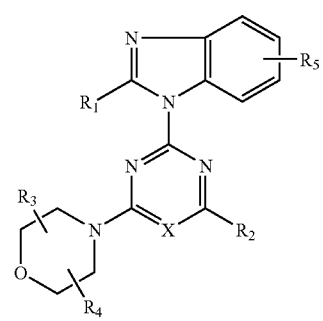

(I)

wherein

X represents a nitrogen atom or CH;

$R_1$ represents $CH_nF_{3-n}$, wherein n is 1 or 2, a hydroxy $C_1$-$C_6$ alkyl, or $NHR_6$, wherein $R_6$ represents a hydrogen atom or COR, wherein R represents a hydrogen atom, a $C_1$-$C_6$ alkyl or a $C_1$-$C_6$ alkoxy;

$R_2$ represents a morpholino which may be substituted with one to four $C_1$-$C_6$ alkyls, a thiomorpholino, a piperidino, a pyrrolidinyl which may be substituted by a hydroxy $C_1$-$C_6$ alkyl, an oxazolidinyl which may be substituted by one or two $C_1$-$C_6$ alkyls or tetrahydro-1,4-thiazin-1-oxo-4-yl;

$R_3$ and $R_4$ each represent a hydrogen atom or a $C_1$-$C_6$ alkyl; and $R_5$ represents a hydrogen atom, an amino or a hydroxyl.

2. A composition consisting of a compound represented by the following formula I, and a pharmaceutically acceptable diluent or carrier:

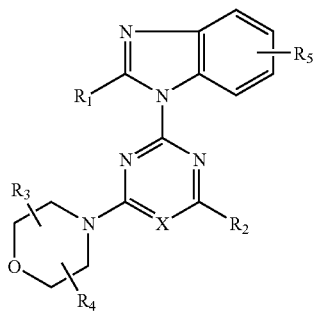

wherein X represents a nitrogen atom or CH;
  $R_1$ represents $CH_nF_{3-n}$, wherein n is 1 or 2, a hydroxy $C_1$-$C_6$ alkyl, or $NHR_6$, wherein $R_6$ represents a hydrogen atom or COR, wherein R represents a hydrogen atom, a $C_1$-$C_6$ alkyl or a $C_1$-$C_6$ alkoxy;
  $R_2$ represents a morpholino which may be substituted with one to four $C_1$-$C_6$ alkyls, a thiomorpholino, a piperidino, a pyrrolidinyl which may be substituted by a hydroxy $C_1$-$C_6$ alkyl, an oxazolidinyl which may be substituted by one or two $C_1$-$C_6$ alkyls or tetrahydro-1,4-thiazin-1-oxo-4-yl;
  $R_3$ and $R_4$ each represent a hydrogen atom or a $C_1$-$C_6$ alkyl; and
  $R_5$ represents a hydrogen atom, an amino or a hydroxyl.

3. The composition according to claim 1, wherein $R_1$ is difluoromethyl.

4. The composition according to claim 2, wherein $R_1$ is difluoromethyl.

5. The composition according to claim 1, wherein $R_1$ is difluoromethyl, $R_2$ is morpholino which may be substituted with one to three methyl and $R_3$ and $R_4$ each are hydrogen atom or methyl.

6. The composition according to claim 2 wherein $R_1$ is difluoromethyl, $R_2$ is morpholino which may be substituted with one to three methyl and $R_3$ and $R_4$ each are hydrogen atom or methyl.

7. The composition according to claim 1, wherein $R_1$ is difluoromethyl, $R_2$ is morpholino which may be substituted with one to three methyl, $R_3$ and $R_4$ each are hydrogen atom and $R_5$ is amino or hydroxyl.

8. The composition according to claim 2, wherein $R_1$ is difluoromethyl, $R_2$ is morpholino which may be substituted with one to three methyl, $R_3$ and $R_4$ each are hydrogen atom and $R_5$ is amino or hydroxyl.

9. The composition according to claim 1, wherein $R_1$ is hydroxymethyl.

10. The composition according to claim 2, wherein $R_1$ is hydroxymethyl.

11. The composition according to claim 1, wherein $R_1$ is hydroxymethyl, $R_2$ is morpholino which may be substituted with one or two methyl and $R_3$ and $R_4$ each are hydrogen atom or methyl.

12. The composition according to claim 2, wherein $R_1$ is hydroxymethyl, $R_2$ is morpholino which may be substituted with one or two methyl and $R_3$ and $R_4$ each are hydrogen atom or methyl.

13. The composition according to claim 1, wherein $R_1$ is amino, formylamino or acetylamino.

14. The composition according to claim 2, wherein $R_1$ is amino, formylamino or acetylamino.

15. The composition according to claim 1, wherein $R_1$ is amino, formylamino or acetylamino, $R_2$ is morpholino which may be substituted with one or two methyl, and $R_3$ and $R_4$ each are hydrogen atom.

16. The composition according to claim 2, wherein $R_1$ is amino, formylamino or acetylamino, $R_2$ is morpholino which may be substituted with one or two methyl, and $R_3$ and $R_4$ each are hydrogen atom.

\* \* \* \* \*

UNITED STATES PATENT AND TRADEMARK OFFICE
CERTIFICATE OF CORRECTION

PATENT NO. : 7,307,077 B2
APPLICATION NO. : 11/478647
DATED : December 11, 2007
INVENTOR(S) : Seiichiro Kawashima et al.

It is certified that error appears in the above-identified patent and that said Letters Patent is hereby corrected as shown below:

Column 10, line 3, "tumor in mutant BALA/c nude mice."
should read -- tumor in mutant BALB/c nude mice. --.

Signed and Sealed this

Thirtieth Day of September, 2008

JON W. DUDAS
*Director of the United States Patent and Trademark Office*